United States Patent [19]

Meltzer

[11] Patent Number: 5,221,679
[45] Date of Patent: Jun. 22, 1993

[54] METHOD OF TREATING THERAPY RESISTANT SCHIZOPHRENIA WITH MELPERONE (R-FLUORO-Y-METHYL-PEPERIDINO-BUTYROPHRENONE)

[75] Inventor: Herbert Y. Meltzer, Shaker Heights, Ohio

[73] Assignee: Case Western Reserve University, Cleveland, Ohio

[21] Appl. No.: 852,742

[22] Filed: Mar. 16, 1992

Related U.S. Application Data

[63] Continuation of Ser. No. 572,499, Aug. 23, 1990, abandoned.

[51] Int. Cl.$^5$ .............................................. A61K 31/445
[52] U.S. Cl. .................................................... 514/317
[58] Field of Search ....................... 514/277, 279, 317

[56] References Cited

U.S. PATENT DOCUMENTS

| | | | |
|---|---|---|---|
| 3,978,216 | 8/1976 | Fuxe | 514/225.5 |
| 4,084,000 | 4/1978 | Fuxe | 514/567 |
| 4,284,638 | 8/1981 | Waldmeier | 514/824 |
| 4,808,630 | 2/1989 | Straw | 514/317 |

OTHER PUBLICATIONS

C.A. 112: (5) 30494n (1990).
The Merck Index—Eleventh Edition (1989)—#2421.
N. C. Andreason and S. O. Olsen, "Negative v. Positive Schizophrenia", *Archives General Psychiatry*, 1982, 39:789–794.
J. Endicott and R. L. Spitzer, "A Diagnostic Interview", *Archives of General Psychiatry*, 1978, 35:837–844.
S. Gershon, "Update on Drug Development", *Psychopharmacology Bulletin*, 1980 16(3):32–35.
R. Grohmann et al., "Adverse Effects of Clozapine" *Physcopharmacology*, 1989, Supplement to vol. 9:S101–S104.
H. P. Hippus, "The History of Clozapine", *Psychopharmacology*, Supplement to vol. 99: S3–S5 1989.
J. M. Kane, "Treatment of Schizophrenia", *Special Report: Schizophrenia*, 1987, N.I.M.H., Treatment of Schizophrenia, in: *Schizophrenia Bulletin*, 13:133–156, 1987.
J. M. Kane and J. Lieberman, "Maintenance Pharmacotherapy and Schizophrenia", *Pharmacotherapy: The Third Generation of Progress*, 1987, ed. H. Y. Meltzer, Raven Press, New York, pp. 1103–1109.
J. E. Overall and D. R. Gorham, "The Brief Psychiatric Rating Scale", *Psychological Reports*, 1962, 10:799–812.
*Diagnostic and Statistical Manual of Mental Disorders* (3rd Ed.), American Psychiatric Assoc., Washington, D.C., 1987, pp. 187–198.
C. A. Altar et al., "Dopamine Neurochemical Profile of Atypical Antipsychotics Resembles that of D-1 Antagonists", *Archives of Pharmacology*, 1988, 388:162–168.
I. Christensen, et al., "Additional Studies on Side Effects of Melperone in Long-term Therapy for 1-20 Years in Psychiatric Patients", *Arzneim.-Forch./Drug Research*, 1986, 36:855–860.
G. A. Gudelsky, et al., "Neuroendocrine Effects of Typical and Atypical Antipsycotics in the Rat", *Psychopharmacology Bulletin*, 1987, 23:483–486.
G. A. Gudelsky, and A. Y. Meltzer, "Activation of Tuberoinfundibular Dopamine Neurons Following the Acute Administration of Atypical Antipsycotics", *Neuropsychopharmacology* 1989, 2:45–51.
J. M. Kane et al., "Clozapine in Treatment-Resistant Schizophrenics", *Psychopharmacology Bulletin*, 1988, 24:62–67.
H. Y. Meltzer et al., "Clozapine-Like Drugs", *Psychopharmacology Bulletin*, 1980, 16(3):32–35.
H. Y. Meltzer et al., "Melperone and Clozapine: Neuroendocrine Effects of Atypical Neuroleptic Drugs", *Acta Psychiatr. Scand.*, 1989, Suppl. 352-24–29.
J. F. Nash et al., "Antagonism of Serotonin Receptor Mediated Neuroendocrine and Temperature Response by Atypical Neuroleptics in the Rat", *European Journal of Pharmacology*, 1988, 151:462–469.

*Primary Examiner*—Frederick E. Waddell
*Assistant Examiner*—T. J. Criares
*Attorney, Agent, or Firm*—Pravel, Hewitt, Kimball & Krieger

[57] ABSTRACT

The invention relates to a method of treating therapy-resistant schizophrenia which includes administering a therapeutically effective amount of melperone (4-fluro-γ-(4-methyl-piperidino)-butyrophenone) or an acceptable acid salt thereof.

5 Claims, No Drawings

METHOD OF TREATING THERAPY RESISTANT SCHIZOPHRENIA WITH MELPERONE (R-FLUORO-Y-METHYL-PEPERIDINO-BUTYROPHRENONE)

This is a continuation of co-pending application Ser. No. 07/572,499 filed on Aug. 23, 1990 now abandoned.

FIELD OF THE INVENTION

This invention relates to the treatment of patients suffering from therapy-resistant schizophrenia by administration of the drug melperone (4-fluoro-γ-(4-methyl-piperidino) - butyrophenone).

BACKGROUND OF THE INVENTION

The treatment of schizophrenia remains one of the major challenges of modern-day medicine. Even incremental advances in the safe and effective use of currently available treatments can have a major impact on the lives of schizophrenic individuals and their families. Reducing rates of relapse and rehospitalization by as little as 10 percent per year can have enormous public health implications. (J. M. Kane, *Special Report: Schizophrenia,* 1987, National Institute of Mental Health, in: *Schizophrenia Bull.,* 13:133–156, 1987).

It is estimated that about 2 million Americans suffer from classical schizophrenia. Approximately 200,000 to 400,000 (10–20 percent) of these schizophrenic patients do not respond to treatment with traditional neuroleptics (antipsychotic drugs) and are classified as therapy-resistant schizophrenics.

Data gathered from maintenance medication trials indicate that 20 to 30 percent of patients initially responsive to antipsychotic drugs may relapse during the first year or two of maintenance drug treatment. A proportion of these relapsed patients may contribute to the number of patients refractory to treatment (J. M. Kane, J. Lieberman, *Psychopharmacology.* the Third Generation of Progress, 1987 Ravin Press, ed., H. Y. Meltzer, pp. 1103-1109).

The term "treatment-(or therapy-)-resistant" schizophrenia used in this context describes a particular illness generally understood by a physician skilled in the art. The treatment-resistant schizophrenic patient may be minimally defined as a patient with schizophrenia without marked symptomatic relief from two treatment periods with two neuroleptic agents from different chemical classes. Clinical research has suggested that neuroleptic-resistant patients suffer from an illness which is characterized by pharmacodynamic, psychological, and physiological properties which differ from those of the neuroleptic-responsive patient. Thus, therapeutic agents known to be effective in the treatment of schizophrenia are not useful in the treatment of therapy-resistant schizophrenia.

In general, the phenothiazines (e.g., chloropromazine) and the butyrophenones (e.g., haloperiodol) constitute the classical neuroleptics used in the treatment of schizophrenia to which the therapy-resistant patient does not respond. More effective pharmacotherapy for the treatment of therapy-resistant schizophrenia has not been developed in the more than three decades since the introduction of the first effective neuroleptic drugs.

Thus far, the only drug approved for clinical use in treating therapy-resistant schizophrenic patients is clozapine, which was approved by the FDA in September 1989 for this particular use. Clozapine, belonging to the chemical class of dibenzodiazepines, was developed in 1966. Agranulocytosis, a potentially fatal drop in white blood cells, is a very dangerous side effect which occurs in 1-2 percent of clozapine-treated patients. Because of this harmful side effect, clozapine has not been used in many countries and for a time was withdrawn from clinical research (H. Hippius, *Psycopharmacology,* 1989, Supplement to Vol. 99 pp. S3–S5; R. Grohmann et. al., *Psycopharmacology,* 1989, Supplement to Vol. 99, pp. S101–S104).

The fact that clozapine now has been accepted by the FDA for treating therapy-resistant schizophrenic patients despite the occurrence of such serious adverse side effects, underlines the urgent need for alternative drugs to treat the therapy-resistant schizophrenic patients. Moreover, there is a need for a method of treating these patients with a drug that does not give rise to potentially fatal adverse reactions.

SUMMARY OF THE INVENTION

It has now unexpectedly been found that melperone, 4-fluoro-γ-(4-methyl-piperidino)-butyrophenone, a psychotropic drug developed in the late 1950s by Hernestam et al. (U.S. Pat. No. 3,816,433), is effective in patients suffering from treatment-resistant schizophrenia. Chemically, melperone is a butyrophenone, and is quite different from clozapine the only drug currently useful for the treatment of therapy-resistant schizophrenia.

DETAILED DESCRIPTION OF THE INVENTION

Neuroleptic drugs are used to reduce psychotic symptoms. However, treatment-resistant schizophrenic patients do not respond to typical neuroleptic drugs. Once treatment with two or more of the standard neuroleptic drugs has been tried and failed, the illness is defined as treatment-resistant schizophrenia.

Melperone (4-fluoro-γ-(4-methyl-piperidino)-butyrophenone) is effective in treating therapy-resistant schizophrenia. Melperone may be effective in a certain subpopulation of the treatment-resistant schizophrenic patients due to its chemical structure and pharmacological properties.

Melperone, because its use is associated with a low incidence of EPS (extrapyramidal symptoms) and because its use does not cause increased levels of prolactin, was previously thought to be ineffective in the treatment of schizophrenia. However, clozapine, a drug known to be effective in the treatment of therapy-resistant schizophrenia, also does not cause EPS or increased serum prolactin (S. Gershon, *Psychopharmacology Bulletin,* 1980, 15(3):32–35). Unlike typical neuroleptic drugs, both melperone and clozapine appear to affect only the mesolimbic ($A^{10}$) dopamine neurons and do not inactivate the nigrostriatal ($A^9$) dopamine neurons. Both melperone and clozapine treatment causes an increase in hypothalamic DA turnover, and an elevation of serum corticosterone in rats.

There are differences between the activities of melperone and clozapine. Clozapine-treated rats display down-regulated cortical serotonin 2 receptors after 21 days of treatment, whereas melperone has no effect on serotonin 2 receptors. A fatal side effect of clozapine, agranulocytosis, occurs in 1-2 percent of all clozapine-treated patients. In all the years of melperone's widespread use in Europe there has not been one reported case of agranulocytosis associated with its use alone. Thus melperone is a very safe drug compared to clozapine which makes it an interesting alternative for treatment of therapy-resistant schizophrenic patients.

Melperone which is discussed above is a butyrophenone of the following formula:

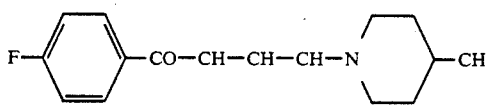

and may be a free base or an acceptable acid salt thereof such as melperone hydrochloride.

A therapeutically effective amount of melperone for use in the treatment of therapy-resistant schizophrenia would be from about 50 to about 1200 mg, depending upon many factors, including the specific condition of the patient, the age and weight of the patient, and the patient's response to the medication. Daily dosages should preferably range from about 200 to 600 mg of melperone. The exact individual dosage, as well as the daily dosage, will be determined according to standard medical principles under the direction of a physician. The appropriate dosage will be the minimal dose which is effective in causing a significant reduction in psychopathology, as determined by clinical improvement or by a reduction in the BPRS score.

The active ingredient, melperone, may be administered to a patient in need of such treatment according to usual routes of administration and in usual forms. These include solutions, suspensions, emulsions, tablets, capsules, and powders prepared in pharmaceutically acceptable carriers for oral administration or sterile solutions for parenternal administration.

Various additives to enhance the stability or ease of administration of the drug are contemplated. The pharmaceutical composition may also contain additional therapeutically useful substances other than melperone.

The following examples are intended to illustrate the present invention without limiting the scope thereof.

EXAMPLES

Example 1

Preparation of a Melperone Tablet

Melperone tablets were prepared having the following composition:

| | |
|---|---|
| Melperone hydrochloride | 100 mg |
| Lactose | 155 mg |
| Cellulose | 40 mg |
| Talc | 7.5 mg |
| Stearic acid powder | 7.5 mg |
| Silicone dioxide | 0.5 mg |
| Polyvinylpyrrolidone | 10 mg |

The tablet may additionally be provided with a standard coating. A standard sucrose coating was used in the following studies.

Example 2

Clinical Trial of Melperone in Treatment-Resistant Schizophrenic Patients

Experimental studies were conducted to evaluate the efficacy of melperone in the treatment of patients suffering from therapy-resistant schizophrenia or other psychotic disorders. The study utilized patients who had experienced an inadequate clinical response to, or adverse effects from, clozapine or patients who qualified for clozapine therapy as non-responders to typical treatments but who refused to take clozapine due to fear of agranulocytosis.

Patient Population

Participants in this study were in- or out-patients with diagnoses of schizophrenia, schizo-affective disorder, delusional disorder or psychotic disorder not otherwise specified, according to the criteria of the *Diagnostic and Statistical Manual of Mental Disorders,* III Edition (Revised 1987, American Psychiatric Association). Participants had also shown poor response to, or had suffered adverse effects from, clinically adequate trials of two or more typical neuroleptic drugs and/or clozapine.

Poor response was defined as follows: delusions, hallucinations, thought disorder, grossly bizarre behavior or negative symptoms (blunted affect, withdrawal, loss of motivation) which had persisted for at least 12 months despite treatment with at least two different typical neuroleptic drugs at a dose equivalent to 800 mg per day of chloropromazine, and up to 300 mg per day of clozapine. If the attempt to use clozapine was aborted because of side effects, the dosage requirement was waived. The Brief Psychiatric Rating Scale (BPRS) total for these patients was greater than 30 while taking neuroleptic drugs.

Participants included males and females, 18 to 75 years of age. Females of childbearing potential were included if they were on an adequate birth control regime and had no plans to become pregnant. Patients with current diagnoses of alcohol abuse, substance abuse, or organic brain disease, and patients with clinically significant medical illnesses requiring treatment were excluded.

Specific Protocol—Psychiatric Screening

Potential participants were clinically evaluated with a Schedule for Affective Disorders and Schizophrenia (SADS), (Endicott and Spitzer, *Arch. Gen. Psych.,* 35: 837–844, 1978) and the Brief Psychiatric Rating Scale, (BPRS), (Overall and Gorham, *Psychol. Rep.* 10:799–812, 1962.) A psychiatric and neuroleptic treatment history was obtained from the patient, informants and medical records. If at the time of evaluation, the patient had delusions, hallucinations, thought disorder or severe negative symptoms, and if the treatment history revealed that there had been two trials of at least six weeks duration with two neuroleptic drugs of two different classes, and the patient had received one of these drugs at a dose equivalent to chloropromazine, 800 mg per day, or if the patient failed to respond to clozapine at doses of up to 300 mg per day or for more than at least six weeks or could not tolerate clozapine due to side effects, they were included as eligible for melperone.

In order to prevent adverse reactions due to the interaction between different medications, all patients went through a 5 to 21 day washout period depending upon their condition. During this washout period, the patients were given a placebo. Patients who had poor clinical response to or adverse side effects to clozapine were withdrawn from the clozapine treatment at least one week, then treated with a typical neuroleptic of the clinician's choice for approximately three weeks, then withdrawn from all major neuroleptic medications for 5 to 21 days prior to the treatment with melperone.

Medical Screening

Eligible patients were given a complete physical examination. Laboratory testing included ECG, SMA-20, CBC and urinalysis. These tests were repeated quarterly, or at the time of termination of the study. Any patient having evidence of significant medical illness or having a clinically significant abnormal laboratory test result was excluded from the study.

Melperone Treatment

Melperone tablets (containing 25 or 100 mg melperone) were given starting at 50 mg daily. The dose was increased by 50 mg per day as rapidly as needed to control psychotic symptoms or agitation up to a maximum of 400 mg per day. Treatment continued for a minimum of 20 weeks unless the patient deteriorated from the previous best level of response. If the patient showed less than 50 percent improvement in BPRS or negative symptom scores at the end of the 20 weeks of treatment they were withdrawn from the study. If the patient showed 50 percent of more improvement, they were permitted to remain on melperone for an indefinite period of time.

During the melperone treatment phase, patients had blood drawings weekly for the first six weeks and monthly thereafter for determination of serum levels of prolactin and homovanillic acid, to determine the effects of melperone on the neuroendocrine and dopaminergic systems.

Ratings of Psychopathology

Patients were evaluated with the SADS; BPRS; Scale for the Assessment of Negative Symptoms (SANS); Scale for the Assessment of Positive Symptoms (SAPS), (Andreasan, *Arch. Gen. Psych.*, 39:784–780, 1982); and the Clinical Global Impressions (CGI) scale. Patients were evaluated by means of the change version of the SADS (SADS-C) and the CGI at the end of the drug-free period and weekly for the duration of the study. At the end of 6, 12, and 18 weeks, the SANS and SAPS were repeated. Evaluations were conducted by trained raters, who were Masters level psychologists. Comparisons of the ratings were then reported as no change, minimal change, much improved, or very much improved by the raters. Those with no change are categorized as non-responders, those with any change from minimal to very much improved are categorized as responders.

The Simpson-Angus scale (Simpson and Angus, 1962) was administered weekly for the evaluation of extrapyramidal Symptoms (EPS). Neurological, cardiovascular, gastrointestinal, and other side effects were monitored at all follow-up visits.

RESULTS

TABLE I

| Melperone Clinical Criteria Responders Clinical Global Improvement | | |
|---|---|---|
| (6 weeks) | N | % |
| No Change | 9 | 45 |
| Minimal Improvement | 2 | 10 |

TABLE I-continued

| Melperone Clinical Criteria Responders Clinical Global Improvement | | |
|---|---|---|
| (6 weeks) | N | % |
| Much Improved | 3 | 15 |
| Very Much Improved | 6 | 30 |

TABLE II

| Melperone Clinical Criteria Responders | | |
|---|---|---|
| (3 months) | N | % |
| Drop-outs | 3 | 12.5 |
| No Response | 9 | 37.5 |
| Response, But Relapse | 2 | 8.5 |
| Continuing Responders | 10 | 41.7 |

TABLE III

| Clozapine Versus Melperone Response Rate for Patients Treated Greater Than Three Months ($\geq$ 20 percent decrease in total BPRS) | | |
|---|---|---|
|  | Clozapine | Melperone |
| Responders | 6 (35.2%) | 4 (33%) |
| Non-Responders | 11 (64.7%) | 8 (67%) |

TABLE IV

| Side Effects of Melperone | | |
|---|---|---|
|  | Non-Responders (20) | Responders (7) |
| Akathesia | 1 | 2 |
| Hypotension | 1 | 1 |
| Somatic Complaints | 0 | 1 |
| Sedation | 1 | 0 |
| Seizures | 0 | 0 |
| Weight Gain | 0 | 0 |
| Tachycardia | 0 | 0 |
| Other EPS | 0 | 0 |

Thus, it is to be understood that the invention is not to be limited to the exact details of the study, composition of drug or procedures described, as obvious modifications will be apparent to one skilled in the art.

We claim:

1. A method of treating a patient suffering from therapy-resistant schizophrenia comprising administering to the patient a therapeutically effective amount of melperone (4-fluro-γ-(4 methyl-piperidino)-butyrophenone) of the formula:

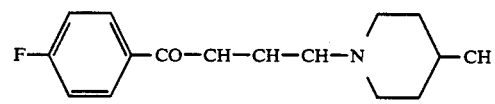

or an acceptable acid salt thereof.

2. The method of claim 1, wherein the therapeutically effective amount ranges from about 50 to about 1200 mg daily.

3. The method of claim 1, wherein the therapeutically effective amount ranges from about 200 to about 600 mg daily.

4. The method of claim 1, wherein the administration of melperone is continued daily for a period of six weeks or longer.

5. The method of claim 1 wherein the effective amount of melperone is dispersed within a pharmaceutically acceptable carrier.

* * * * *